United States Patent [19]

Aonuma

[11] Patent Number: 4,745,101
[45] Date of Patent: May 17, 1988

[54] NOVEL PEPTIDE HAVING DENTINAL FLUID TRANSPORT-STIMULATING ACTIVITY

[75] Inventor: Shigeru Aonuma, Gotenba, Japan

[73] Assignee: Teikoku Hormone Mfg. Co., Ltd., Tokyo, Japan

[21] Appl. No.: 856,021

[22] Filed: Apr. 25, 1986

[30] Foreign Application Priority Data

Apr. 26, 1985 [JP] Japan .................................. 60-88862

[51] Int. Cl.$^4$ ......................... A61K 37/02; C07K 7/08
[52] U.S. Cl. ....................................... 514/13; 530/326
[58] Field of Search ........................... 530/326; 514/13

[56] References Cited

PUBLICATIONS

Yamamoto et al., Chem. Pharm. Bull., vol. 34(9), pp. 3803–3811 (1986).

Yamamoto et al., Chemical Abstracts, vol. 106, No. 46793w (1987).

Primary Examiner—John Kight
Assistant Examiner—Christina Chan
Attorney, Agent, or Firm—Wenderoth, Lind & Ponack

[57] ABSTRACT

A peptide having the amino acid sequence represented by the following formula $$\underset{1}{\text{Gly}}-\text{Val}-\text{Ile}-\text{Ala}-\text{Trp}-\text{Glu}-\text{Leu}-\text{Gln}-\text{His}-\underset{10}{\text{Asn}}-\text{Glu}-$$
$$-\text{Pro}-\text{Gly}-\text{Arg}-\text{Lys}-\text{Asp}-\text{Ser}-\text{Thr}-\text{Ala}-\underset{20}{\text{Gly}}.$$

This peptide can be obtained by extracting from a salivary gland of rats and is useful for preventing or treating caries.

3 Claims, No Drawings

NOVEL PEPTIDE HAVING DENTINAL FLUID TRANSPORT-STIMULATING ACTIVITY

This invention relates to a novel peptide having dentinal fluid transport-stimulating activity obtained from salivary glands, particularly the parotid gland, of rats.

It has already been known that when a hypothalamic extract from a rabbit is administered to a rat whose parotid gland has been extracted, transport of a body fluid from the dental pulp to the odontoblastic tubules in the dentin is not observed, but that fluid transport is observed when the hypothalamic extract is administered together with a parotid tissue extract of pigs. This is considered to show that the hypothalamic factor acts directly on the parotid gland, and the stimulation of fluid transport from the dental pulp to the odontoblastic tubules in the dentin depends upon the parotid gland. Steinman et al., in the course of studies on a caries-inducing substance and the occurrence of dental caries in rats, isolated a dentinal fluid transport-stimulating substance from the parotid gland of pigs, and determined it to be a protein which has a molecular weight of 8,100 and an isoelectric point of pH 7.5, contains 46% of glycine and 28% of proline and hardly has an ultraviolet absorption ~Endocrinology, 83, 807 (1968); Endocrinology, 106, 1994 (1980)]. Steinman et al. also reported that administration of this active substance to rats increased supply of nutrients to the teeth, thereby promoting growth of the teeth, strengthening the dental structure and inhibiting the occurrence of dental caries.

The present inventor postulated the presence of a substance having the activity of stimulating dentinal fluid transport (to be referred to as the "DFT-stimulating substance") in salivary glands, particularly the parotid gland, of rats as in pigs, and has extensively worked on the determination of the presence of this substance in the parotid gland of rats. As a result, the inventor succeeded in determining its presence, and on further investigations on its isolation, isolated a DFT-stimulating substance of a very high purity and determined its chemical structure (amino acid sequence).

According to this invention, there is provided a peptide having DFT-stimulating activity which is represented by the following amino acid sequence 1                                              10
Gly—Val—Ile—Ala—Trp—Glu—Leu—Gln—His—Asn—Glu—

20
—Pro—Gly—Arg—Lys—Asp—Ser—Thr—Ala—Gly.

The peptide provided by this invention has the following physicochemical properties.

(1) Ultraviolet absorption spectrum

Maximum absorption wavelength ($\lambda_{max}$)=280 nm

The maximum absorption wavelength is measured by using a spectrophotometer (Model 210 made by Shimadzu Seisakusho) with a light path length of 1 cm on 0.80 mg of a sample dissolved in 1 ml of physiological saline.

(2) Solubility

Soluble in water and physiological saline. Insoluble in acetone.

(3) Color reaction

Ninhydrin reaction: positive
Biuret reaction: positive
Sakaguchi reaction: positive (4) Distribution coefficient (Kav)

This is the distribution coefficient between a gel layer and a liquid layer in gel filtration, and is calculated from the following equation.

$$Kav = \frac{Ve - Vo}{Vt - Vo}$$

Vt=the total volume of the gel layer and the liquid layer
Ve=the amount of the eluent
Vo=the amount of the solvent outside the gel particles When Sephadex G-25 (a product of Pharmacia Fine Chemicals) is used as a gel filtration material and 0.05M phosphate buffer (pH 7.2) is used as the eluent, the active peptide of this invention has a Kav value of about 0.44.

As stated above, the DFT-stimulating substance which Steinman et al. extracted from the parotid gland of pigs is a substance which has a molecular weight, measured by SDS-polyacrylamide gel disc electrophoresis, of 8,100, an isoelectric point of pH 7.5 and no maximum absorption wavelength ($\lambda_{max}$) in its ultraviolet absorption spectrum and contains 46% of glycine and 28% of proline. As can be clearly seen from the above structural formula and physicochemical properties, the peptide of this invention is evidently different from the DFT-stimulating substance extracted from the parotid gland of pigs at least in molecular weight, amino acid composition and ultraviolet absorption characteristics, and is believed to be a novel substance not described in the prior literature.

The salivary glands, particularly the parotid gland, of mammals secrete salivary gland hormone which is a protein and has various excellent physiological activities such as the activity of promoting growth of hard tissues, the activity of activating mesenchymal tissues, the activity of reducing the serum calcium, and the activity of increasing leucocytes, and finds wide applications as a medicine. The present inventor, however, has ascertained that this salivary gland hormone shows no action on the DFT to the odontoblastic tubules in the dentin of rats. It is evident therefore that the DFT-stimulating substance existing in the parotid gland of rats is different from the salivary gland hormone also in respect of action.

The DFT-stimulating activities of the peptide of this invention and the salivary gland hormone were measured by the following method.

Acriflavine hydrochloride as a fluorescent substance was interaperitoneally administered to 5-week old rats at a rate of 5 mg per 100 g of body weight. Immediately then, 0.1 ml of the peptide of this invention or the salivary gland hormone was intravenously administered. Sixteen minutes later, the animals were beheaded. Within one minute after beheading, the upper jaw was removed and frozen. A molar section perpendicular to the occlusal surface was prepared by using a microtome. Under a fluorescent microscope, the migration of the fluorescent substance to the odontoblastic tubules in the dentin was observed. The results was indicated by positive (+)

when the migration was suffiient, or negative (−) when the migration was insufficient or failed.

The results of a comparison of the DFT-stimulating effect of the peptide of this invention extracted from the rat's parotid gland with that of the salivary gland hormone are shown in Table 1.

TABLE 1

| Sample | Dosage (ng/kg) | Number of rats where DFT occurred fully/ total number of rats tested | Rating |
|---|---|---|---|
| Peptide | 1,000 | 8/8 | (+) |
| of the | 100 | 8/8 | (+) |
| invention | 10 | 7/8 | (+) |
| Salivary | 1,000 | 0/8 | (−) |
| gland | 100 | 0/8 | (−) |
| hormone | 10 | 0/8 | (−) |

The peptide of this invention can be produced from salivary glands, for example the parotid gland, of rats by a process which comprises (a) a step of acidifying an aqueous extract of a salivary gland of rats to a pH of 4.5 to 5.5 and removing the resulting precipitate, (b) a step of removing components having a molecular weight of at least 30,000 on a molecular sieve and again subjecting the residue to a molecular sieve to collect fractions having a molecular weight of 1,000 to 3,500, and (c) a step of subjecting the resulting fractions to cation exchange and two-dimensional paper chromatography-high voltage electrophoresis to collect a fraction having a molecular weight of about 2,200.

Extraction of the salivary gland of rats with water can be carried out by methods known per se. For example, A fresh sample taken from a salivary gland, for example, the parotid gland, of rats is cut to small pieces, and about 10 times its amount of cold acetone is added. With cooling, the mixture is stirred for one hour and then filtered to defat the gland, followed successively by air drying and drying under reduced pressure to obtain an acetone dried powder. Water is added to the acetone dried powder in an amount of about 10 times the volume of the latter. The pH of the mixture is adjusted to a value in the vicinity of neutrality (pH 6.5–7.5), preferably 7.0, with an alkali such as sodium hydroxide, sodium carbonate or sodium hydrogen carbonate, and extraction is carried out with stirring. Advantageously, the stirring is carried out generally under cooling, preferably at 0° to 5° C., for a period of several hours, usually 2 to 3 hours, after optionally adding an antiseptic (such as toluene). The stirred suspension is subjected to a centrifugation treatment (for example, at 10,000 for 20 minutes) to separate the aqueous extract.

On the other hand, the residue may be discarded as such, or as required, may be subjected to the same extracting operation as above a desired number of times (usually once or twice).

When the pH of the aqueous extract after removal of the residue is adjusted to 4.5–5.5, preferably about 5.0, with an inorganic acid such as hydrochloric acid, a precipitate forms. Desirably, by allowing the extract to stand further for several hours to one day under cooling, (preferably maintained at about 0° to 5° C. in a refrigerator), the precipitation is completed.

The precipitate is centrifuged (for example, at 10,000 rpm for 15 minutes), and the supernatant is separated and recovered.

The recovered supernatant, as required, is concentrated to a suitable amount, for example, to an amount about 1/10 of the original amount by such means as concentration under reduced pressure, and then subjected to a molecular sieving operation using a flat membrane or hollow fibrous memberane such as an ultrafiltration membrane or an ultrafiltration fiber. The fractionation operation can be effected by ultrafiltration using an ultrafiltration membrane or ultrafiltration fiber with a fractionating molecular weight of 5,000 to 50,000, preferably 30,000. For example, Diaflo PM-30 (retention limit: 30,000; a product of Amicon Company) may be used as the ultrafiltration membrane. An example of the ultrafiltration fiber is Hollow Fiber HIP 30 (retention limit: 30,000; a product of Amicon Company).

In the case of using the ultrafilration membrane, the supernatant obtained above is put into a stirred cell (Model 202 made by Amicon Company) equipped with Diaflo PM-30 for example, and can be fractionated by filtering it while it is pressed by nitrogen gas under 2 kg/cm². In the case of using the ultrafiltration fiber, the supernatant is stirred at high speeds in, for example, hollow fibers loaded in an ultrafiltration device (Model DC4 made by Amicon Company) whereby the same reactions as in the case of using the ultrafiltration membrane can be obtained.

As a result, a solution containing an active component stripped of components having a molecular weight of at least about 30,000 can be obtained.

The resulting fraction having a molecular weight of at least 30,000 is optionally concentrated under reduced pressure, and desalted in a Sephadex G-10 column, and again concentrated under reduced pressure. The concentrate is then fractionated by Sephadex LH-20 column chromatography using water, a salt buffer, an organic solvent, or a mixture thereof as an eluent to collect active fractions having a molecular weight of 1,000 to 3,500. The fractions containing the active ingredient are adsorbed on a cation exchange resin, and the resin is eluted to separate the active portion. Examples of cation exchange resins that can be used in this operation are styrene/divinylbenzene type strong acid-type ion exchange resins such as Hitachi Custom ion exchange resin 2611 and Bio-Rad Aminex A-9. In the adsorbing operation, the active component-containing fraction is dissolved in a strongly acidic buffer, preferably a citrate buffer, a glycine buffer or an acetate buffer, and the solution is contacted with the cation exchange resin to adsorb the desired active component on the resin. The resin is then eluted with the aforesaid buffer whose ion concentration is increased by adding an inorganic salt such as sodium chloride or potassium chloride, or a strongly alkaline solution such as sodium hydroxide or potassium hydroxide.

The resulting fraction containing the active component is then desalted on a Sephadex G-10 column, and can be further purified by subjecting it to two-dimensional paper chromatography-high voltage electrophoresis. The two-dimensional paper chromatography-high voltage electrophoresis is a method, also called the "finger print method", whereby peptides are separated by developing a sample two-dimensionally on one piece of filter paper as a support, first subjecting it to chromatography and then to high voltage electrophoresis. This method enables peptides having nearly the same molecular weight but different amino acid sequences to be separated from each other.

Paper chromatography as the first dimension can be carried out by adding the active eluate-containing fraction to a piece of filter paper and developing it with a developing solvent for about 20 hours. The development can be effected by either the ascending or descending method. Examples of the developing solvent include water, alcohols such as methanol and ethanol, phenol, pyridine, ethyl acetate, acetone, diethyl ether, chloroform, and n-hexane. They may be used either singly or in combination. A solvent obtained by saturating a water-immiscible solvent such as butanol with an aqueous solution containing acetic acid, pyridine or the like may also be used. The development results in the separating of various substances from each other.

The high voltage electrophoresis as the second dimension can be carried out in a usual manner by applying an electric field in a direction at right angles to the development in the first procedure to the developed filter paper. A pyridne-acetic acid-water buffer (pH 4–7) which is a volatile buffer, for example, can be used as a buffer in the high voltage electrophoresis. The used of such a buffer is very convenient in extracting an active substance from the filter paper since it can be removed by drying. The extract obtained by the high voltage electrophoresis treatment is subjected to gel fitration using an ultrafiltration membrane with a fractionating molecular weight of 500, such as YC05 (a product of Amicon Company) and Sephadex G-10, or to dialysis using a tube with a fractionating molecular weight of 1,000 such as Spectrapor 7 (a product of Spectrum Medical Industries) to collect a fraction having a molecular weight of about 2,000. The fraction is desalted as required, and lyophilized to give the desired peptide having DFT-stimulating activity.

The amino acid sequence of the resulting peptide can be determined by amino acid analysis, the dansyl-Edman method, the carboxypeptidase Y method and a technique of enzyme decomposition by trypsin.

The peptide of this invention so obtained has DFT activity as shown in Table 1 above, and is expected to be a medicament useful for the prevention and treatment of dental caries. Lactic acid as a microbial metabolite stays on dental deposits formed by the action of a microorganism, and erodes the teeth. The erosion proceeds not only to the enamel but also to the dentin. Factors of the occurrence of dental caries are diverse, and even when the dentin is finally eroded, the tooth has the ability to defend it by forming the second dentin. The supply of a nutrient source is essential to the functional growing of the dentin. A substance stimulating DFT is considered to accelerate the formation of the second dentin.

For use as an agent for preventing or treating dental caries, the peptide of this invention may be formulated into a pharmaceutical preparation suitable for oral or parenteral administration or for administration through the mucosa in accordance with an ordinary formulating method using pharmaceutically acceptable adjuvants. Examples of the adjuvants include an excipient such as starch, lactose, sucrose, mannitol, sorbitol, calcium phosphate or calcium sulfate, a binder such as gelatin, methyl cellulose, a disintegrant such as cellulose and starch, a lubricant such as higher alcohols, talc, magnesium stearate and synthetic aluminum silicate, and an adsorbent or wetting agent such as silicon oxide, glycerol and propylene glycol. For example, an injectable preparation may be formed by dissolving the peptide of this invention in a pharmaceutical formulating liquid such as distilled water for injection, physiological saline, a phosphate buffer, a glycine buffer or a veronal buffer. A lyophilized preparation may be prepared by adding an adjuvant for increasing moldability such as sodium chloride, glycine, lactose, mannitol, sorbitol, sucrose, hydrolyzed starch and dextran to the injectable preparation and lyophilizing the mixture. The peptide of this invention may also be added to usual dentifrices for prevention or treatment of dental caries.

The peptide of this invention can also be expected to stimulate growth of hard tissues in general of animals, particularly ossification.

In using the peptide of this invention as a medicament such as an agent for preventing or treating dental caries of a human, it can be administered orally or parenterally in a dose of 0.001 to 1.0 mg/kg of body weight/day either once or in several divided portions. For incorporation in a dentrifice, its suitable amount is 0.01 to 1.0 mg per gram of the dentrifice. The doses mentioned above are tentative standards, and the medicament can of course be administered in doses exceeding the upper limit depending upon the severity of the patient's condition, the age of the patient, a physician's judgement, etc.

The following Examples illustrate the present invention in greater detail.

EXAMPLE 1

One hundred grams of the parotid gland of rats was minced, and 1 liter of cooled acetone was added. The mixture was stirred for 1 hour with cooling, and then filtered. The excess of acetone was removed by air drying and drying under reduced pressure to form an acetone-dried powder. One liter of water was added to the acetone-dried powder, and the mixture was stirred for 2 hours to extract the powder. The extract was centrifuged at 10,000 rpm for 15 minutes to separate it into a precipitate and a supernatant. To the precipitate was added 300 ml of water, and the mixture was subjected to extracting and centrifuging operations. The resulting supernatant was combined with the supernatant obtained previously, and 1N hydrochloric acid was added to adjust the pH of the mixture to 5.0.

The precipitate was centrifuged at 10,000 rpm for 15 minutes, and the supernatant was adjusted to pH 7.0 with 1N sodium hydroxide. The resulting solution was concentrated under reduced pressure to 100 ml, and filtered on an ultrafiltration membrane having a fractionating molecular weight of 30,000 (PM-30 made by Amicon Company). The filtrate was again concentrated under reduced pressure. The concentrate was desalted and eluted on a Sephadex G-10 column (1.5×90 cm) equilibrated with 0.05M acetate buffer (pH 5.8). The eluate was concentrated under reduced pressure and subjected to gel filtration on a Sephadex LH-20 column (3.8×100 cm) equilibrated with ethanol-acetic acid-water (75:10:95) to collect active fractions with a fractionating molecular weight of 1,000 to 3,500.

The active fractions were charged onto a Hitachi Custom #2611 column (0.9×55 cm) equilibrated with 0.2N sodium citrate buffer (pH 3.25) and the column was washed successively with 0.2N sodium citrate buffer (pH 4.25) and 1.2N sodium citrate buffer (pH 5.28) to remove impurities. Finally, the column was eluted with 0.2N sodium hydroxide, and active fractions eluted were collected.

The active fractions were desalted and concentrated under reduced pressure in the same way as above, and added to filer paper (Toyo Filter Paper No. 50; 42×45 cm). They were developed for 20 hours with a solvent composed of n-butanol, pyridine, acetic acid and water (15:10:3:12), and then subjected to electrophoresis at 150 mA for 90 minutes using a solution composed of pyridine, acetic acid and water (10:0.4:90) as an electrode solution. The active portion on the filter paper was then extracted. The active extract was desalted by an ultrafiltration member having a fractionating molecular weight of 500 (YC05 made by Amicon Company), and then lyophilized to give 0.45 mg of the desired peptide having dentinal fluid transport-stimulating activity.

The peptide was subjected to amino acid analysis by the following method and determined to be a substance having a molecular weight of 2,165 and an amino acid sequence represented by the following formula.

```
1                                          10
Gly—Val—Ile—Ala—Trp—Glu—Leu—Gln—His—Asn—Glu—
                                           20
        —Pro—Gly—Arg—Lys—Asp—Ser—Thr—Ala—Gly.
```

(1) Amino acid analysis

A sample of the above peptide (25 n-moles) was hydrolyzed with 6N hydrochloric acid at 110° C. for 24 hours, and dried under reduced pressure at 50° C. for 15 minutes. To the dry residue was added 0.2M sodium phosphate buffer (pH 6.5) to adjust its pH to 6.5. The mixture was left to stand for 4 hours to oxidize it with air, and then 1N hydrochloric acid was added to adjust the pH to 2. Then, citrate buffer (pH 2.2) was added and the mixture was subjected to analysis.

To analyze Trp, 50 n-moles of the sample was hydrolyzed in 2.5N sodium hydroxide at 110° C. for 20 hours in the presence of 0.2 mg of starch. The product was neutralized with 1N hydrochloric acid and dried under reduced pressure. The resulting product was used for analysis.

The sample was found to have the following amino acid composition (the parenthesized numbers indicate the number of amino acid residues per molecule).

Asp (2), Thr (1), Ser (1), Glu (3), Pro (1), Gly (3), Ala (2), Val (1), Ile (1), Leu (1), Lys (1), His (1), Arg (1), Trp (1).

(2) Amino acid sequence (a) Analysis of N-terminal sequence

The N-terminal sequence was analyzed by the dansyl-Edman method in accordance with the method of Gray et al. [Biochem. J., 89, 379 (1963)]. A sample (50 n-moles) was dissolved in 30 ml of a 50% aqueous solution of pyridine in a ground stopper test tube. Then, 10 microliters of a 20% pyridine solution of phenyl isothiocyanate was added, and nitrogen gas was blown into the test tube for 15 minutes. The test tube was sealed, and the reaction was carried out. One hour later, the reaction mixture was dried under reduced pressure. Ethanol (20 microliters) was added, and again the mixture was dried under reduced pressure. Thereafter, 30 microliters of trifluoroacetic acid was added to hydrolyze the reaction product at 45° C. Thirty minutes later, trifluoroacetic acid was volatilized with nitrogen gas. Water (100 microliters) was added, and the mixture was dried under reduced pressure to remove trifluoroacetic acid completely. The residue was suspended in 100 microliters of water, and extracted three times with 400 microliters of butyl acetate. An aliquot (1 to 5 n-moles) of the resulting aqueous layer was transferred to a separate vessel to be described, and the remainder was lyophilized. Then, the lyophilized product was dissolved in a 50% aqueous solution of pyridine in the same way as at the outset, and again reacted with phenyl isothiocyanate. In this way, the amino acid sequence was analyzed successively from the N-terminus. Dansylation was carried out as follows. A prepared sample was put into a small test tube, and dried under reduced pressure in a desiccator. Ten microliters of 0.2M sodium bicarbonate was added. The mixture was centrifuged, and the supernatant was again dried under reduced pressure. To the dried product was added 1 mg/ml of a dansyl chloride-acetone solution, and the mixture was reacted at 37° C. for 1 hour. After drying under reduced pressure, 500 microliters of 6N hydrochloric acid was added, and the small test tube was sealed up. Hydrolysis was carried out at 105° C. for 18 hours. Asparagine, glutamine and tryptophan were identified directly by the Edman method. Conversion of amino acid to a phenylthiohydantoin (PTH) derivative was carried out as follows. A phenylthiazoline derivative in butyl acetate was dried under reduced pressure and reacted with 1N hydrochloric acid at 80° C. for 10 minutes. The resulting PTH amino acid was extracted with ethyl acetate and developed by using a polyamide sheet.

It was found that the N-terminal pentapeptide was Gly-Val-Ile-Ala-Trp-.

(b) C-terminal sequence analysis

The C-terminal sequence was analyzed by the carboxypeptidase Y method in accordance with the method of Hayashi et al. [J. Biochem., 77, 69 (1975)]. Twelve microliters of carboxypeptidase Y (1 mg/ml) (24 units/mg; a product of Sigma Co.) in 0.05M phosphate buffer (pH 6.5) was added to 75 n-moles of a sample in 150 microliters of 0.05M phosphate buffer. The sample was then reacted with the enzyme at 25° C. After the lapse of 15, 60 and 240 minutes respectively, the reaction was stopped by freezing the reaction mixture at −40° C., and the free amino acids were quantitatively determined.

Gly was rapidly freed by enzymatic digestion with carboxypeptidase Y, and Ala, Thr, Ser and Asp were further freed. At 60 minutes, Lys and Arg were freed. The free amino acids were quantitatively determined in the same manner by using carboxypeptidase A for 15, 30 and 60 minutes. After 60 minutes a trace of Gly was observed. The results show that the C-terminal Gly has a free carboxyl group.

It was found consequently that the C-terminal pentapeptide is -Arg-Lys-Asp-Ser-Thr-Ala-Gly.

Amino acid sequence of a peptide fragment by trypsin decomposition

A sample (2 mg) was dissolved in 200 microliters of 0.2M ammonium bicarbonate, and the pH of the solution was adjusted to 8.2 with dilute aqueous ammonia. Then, 20 micrograms of diphenylcarbamyl chloride (DPCC)-trypsin in 100 microliters of 0.1M calcium chloride (10000 BAEE units/mg; a product of Sigma Co.) was added, and the reaction was carried out at 37° C. Three hours later, the same amount of DPCC-trypsin was again added, and the reaction was continued for 3 hours. Acetic acid was added to adjust the pH of the reaction mixture to 3.0, and the reaction was stopped. The product was recovered as a lyophilized product. The trypsin decomposition product was fractionated into 5 spots by the peptide map method. Each of the spots was cut off, extracted with 0.1N aqueous ammonia, and recovered as a lyophilized product. Each of the products was hydrolyzed with 6N hydrochloric acid, and subjected to amino acid analysis. One was a peptide fragment consisting of the 1st to the 15th amino acids from the N-terminus of a purified sample. Amino acids were identified directly by the Edman method from the N-terminus of the peptide fragment, and it was found that from the 6th amino acid, the sequence is Glu, Leu, Gln, His, Asn, Gln, Pro, Gly. From the C-terminus, amino acids were successively identified as Lys and Arg by the carboxypeptidase Y method.

From the results of (a), (b) and (c), the entire primary structure of the sample was as follows:

1                                          10
Gly—Val—Ile—Ala—Trp—Glu—Leu—Gln—His—Asn—Glu—

20
—Pro—Gly—Arg—Lys—Asp—Ser—Thr—Ala—Gly.

The results well agreed with the results of the amino acid analysis.

The above purified authentic sample showed DFT-stimulating activity in a dose of 30 ng/kg (i.v.) in rats according to the measuring method described hereinabove.

EXAMPLE 2

(1) Injectable preparation (0.05 mg/ampoule)

Sodium chloride (3.5 g) was dissolved in 500 ml of 0.05M acetic acid-sodium acetate buffer, and 25 mg of the peptide obtained in Example 1 was dissolved in the resulting solution. The solution was aseptically filtered by using a membrane filter (0.2 micron), and filled in 1 ml. ampoules. The inside of the ampoules was purged with nitrogen, and then the ampoules were sealed up by fusion.

Five hundred 1 ml. ampoules were obtained.

(2) Capsules (0.5 mg/capsule)

Powdery lactose (50 mg) and 0.5 mg of the active component (peptide) were fully mixed, and pulverized. Mannitol (48.5 mg) and 1 g of magnesium stearate was added and fully mixed. The mixture was filled into capsules.

What is claimed is:

1. A peptide having the amino acid sequence represented by the following formula 1                                          10
Gly—Val—Ile—Ala—Trp—Glu—Leu—Gln—His—Asn—Glu—

20
—Pro—Gly—Arg—Lys—Asp—Ser—Thr—Ala—Gly.

2. The peptide of claim 1 which is isolated from the parotid gland of rats and is substantially pure.

3. A pharmaceutical preparation for preventing or treating caries comprising an effective amount for the prevention or treatment of caries of the peptide of claim 1 and a pharmaceutically acceptable adjuvant.

* * * * *